US00RE47582E

(19) United States
(12) Reissued Patent
Golkowski

(10) Patent Number: US RE47,582 E
(45) Date of Reissued Patent: *Aug. 27, 2019

(54) FREE RADICAL STERILIZATION SYSTEM AND METHOD

(71) Applicant: STERIFRE MEDICAL, INC., Kirkland, WA (US)

(72) Inventor: Czeslaw Golkowski, Ithaca, NY (US)

(73) Assignee: STERIFRE MEDICAL, INC., Kirkland, WA (US)

( * ) Notice: This patent is subject to a terminal disclaimer.

(21) Appl. No.: 15/191,384

(22) Filed: Jun. 23, 2016

Related U.S. Patent Documents

Reissue of:
(64) Patent No.: 8,758,681
Issued: Jun. 24, 2014
Appl. No.: 13/524,380
Filed: Jun. 15, 2012

U.S. Applications:
(63) Continuation-in-part of application No. 12/510,341, filed on Jul. 28, 2009, now Pat. No. 8,221,679.

(51) Int. Cl.
*A61L 2/00* (2006.01)
*A62B 7/08* (2006.01)
(Continued)

(52) U.S. Cl.
CPC ..... *A61L 2/00* (2013.01); *A61L 2/208* (2013.01); *A61L 11/00* (2013.01); *A01N 1/0294* (2013.01);
(Continued)

(58) Field of Classification Search
CPC . A61L 2/208; A61L 2/00; A61L 11/00; A61L 2/22; A61L 2202/11;
(Continued)

(56) References Cited

U.S. PATENT DOCUMENTS 4,863,688 A 9/1989 Schmidt et al.
4,992,247 A 2/1991 Foti
(Continued)

FOREIGN PATENT DOCUMENTS

CA 2735739 1/2011
EP 0298694 1/1989
(Continued)

OTHER PUBLICATIONS

"Ellie. The first ever digital UV sterlizing pod" available at https://www.indiegogo.com/projects/ellie-the-first-ever-digital-uv-sterlizing-pod-baby-technology--2, retrieved from internet Apr. 6, 2017.
(Continued)

*Primary Examiner* — Krisanne M Jastrzab
(74) *Attorney, Agent, or Firm* — Knobbe, Martens, Olson & Bear LLP

(57) ABSTRACT

A free radical sterilization system having a chamber defining a region, and a generator for generating free radical reach effluent from a free radical electric generator and/or a vaporizer. A closed loop circulating system without a free-radical destroyer is provided for supplying the mixture of free radicals from the electric generator mixed with the hydrogen peroxide solution in the form of the effluent to the chamber. The free-radical sterilization system is used in sterilizing items in the chamber and, with an open-bottomed wound chamber, in treating wounds on a body.

37 Claims, 10 Drawing Sheets

(51) Int. Cl.

| | |
|---|---|
| ***A61L 9/00*** | (2006.01) |
| ***F26B 21/06*** | (2006.01) |
| ***F22D 7/00*** | (2006.01) |
| ***H05F 3/00*** | (2006.01) |
| ***B05B 5/12*** | (2006.01) |
| ***B60H 3/02*** | (2006.01) |
| ***A61L 2/20*** | (2006.01) |
| ***A61L 11/00*** | (2006.01) |
| *A61L 2/22* | (2006.01) |
| *A61M 1/00* | (2006.01) |
| *A61L 9/03* | (2006.01) |
| *A61L 9/015* | (2006.01) |
| *B05B 12/14* | (2006.01) |
| *A61L 2/18* | (2006.01) |
| *A01N 1/02* | (2006.01) |

(52) U.S. Cl.

CPC ..... *A61L 2/186* (2013.01); *A61L 2/22* (2013.01); *A61L 9/00* (2013.01); *A61L 9/015* (2013.01); *A61L 9/03* (2013.01); *A61L 2202/11* (2013.01); *A61L 2202/14* (2013.01); *A61L 2202/15* (2013.01); *A61L 2202/26* (2013.01); *A61M 1/0019* (2013.01); *B05B 12/14* (2013.01)

(58) Field of Classification Search

CPC ..... A61L 2202/14; A61L 2202/15; A61L 2202/26; A61L 9/03; A61L 9/015; A61L 9/00; A61L 2/186; A61M 1/0019; B05B 12/14; A01N 1/0294

See application file for complete search history.

(56) References Cited

U.S. PATENT DOCUMENTS

| | | | | |
|---|---|---|---|---|
| 5,087,418 | A * | 2/1992 | Jacob | A61L 2/14 204/164 |
| 5,173,258 | A | 12/1992 | Childers | |
| 5,209,411 | A * | 5/1993 | Dineley | A61L 11/00 241/17 |
| 5,445,792 | A | 8/1995 | Rickloff et al. | |
| 5,508,009 | A | 4/1996 | Rickloff et al. | |
| 5,534,221 | A | 7/1996 | Hillebrenner et al. | |
| 5,578,280 | A | 11/1996 | Kazi et al. | |
| 5,779,973 | A | 7/1998 | Edwards et al. | |
| 5,792,435 | A | 8/1998 | Mueller et al. | |
| 6,073,627 | A | 6/2000 | Sunnen | |
| 6,077,480 | A | 6/2000 | Edwards et al. | |
| 6,113,851 | A | 9/2000 | Soloshenko et al. | |
| 6,156,267 | A | 12/2000 | Pai et al. | |
| 6,187,266 | B1 | 2/2001 | Lin et al. | |
| 6,329,628 | B1 | 12/2001 | Kuo et al. | |
| 7,091,441 | B1 | 8/2006 | Kuo | |
| 7,186,374 | B2 | 3/2007 | Zelina et al. | |
| 7,621,985 | B1 | 11/2009 | Kuo | |
| 7,777,151 | B2 | 8/2010 | Kuo | |
| 7,803,315 | B2 | 9/2010 | McDonnell et al. | |
| 7,880,887 | B2 | 2/2011 | Olson et al. | |
| 8,115,135 | B2 | 2/2012 | Kuo | |
| D656,622 | S | 3/2012 | Gasser et al. | |
| 8,153,078 | B2 | 4/2012 | Bacik et al. | |
| 8,221,679 | B2 | 7/2012 | Golkowski | |
| 8,444,919 | B2 | 5/2013 | Erickson | |
| 8,551,399 | B2 | 10/2013 | Shannon et al. | |
| 8,591,807 | B2 | 11/2013 | Berentsveig et al. | |
| 8,591,808 | B2 | 11/2013 | Berentsveig et al. | |
| 8,636,951 | B2 | 1/2014 | Shannon et al. | |
| 8,658,089 | B2 | 2/2014 | Berentsveig et al. | |
| 8,668,882 | B2 | 3/2014 | Berentsveig | |
| 8,758,681 | B2 | 6/2014 | Golkowski | |
| 8,927,896 | B2 | 1/2015 | Kuo | |
| 8,974,737 | B2 | 3/2015 | Erickson | |
| 8,977,115 | B2 | 3/2015 | Penman, Jr. | |
| 8,992,829 | B2 | 3/2015 | Shannon et al. | |
| 9,010,574 | B2 | 4/2015 | Gasser et al. | |
| 9,027,385 | B2 | 5/2015 | Hingley et al. | |
| 9,050,385 | B2 | 6/2015 | Weinberger et al. | |
| 9,138,005 | B2 | 9/2015 | Berentsveig et al. | |
| 9,192,164 | B2 | 11/2015 | Berentsveig et al. | |
| 9,226,495 | B2 | 1/2016 | Berentsveig et al. | |
| 9,241,491 | B2 | 1/2016 | Berentsveig et al. | |
| 9,333,275 | B2 | 5/2016 | Berentsveig | |
| 9,849,204 | B2 | 12/2017 | Taggart | |
| 2002/0068028 | A1 | 6/2002 | Hight, III | |
| 2005/0063882 | A1 | 3/2005 | Centanni et al. | |
| 2005/0129571 | A1 | 6/2005 | Centanni | |
| 2005/0260097 | A1 | 11/2005 | Williams et al. | |
| 2006/0027539 | A1 * | 2/2006 | Golkowski | A61L 2/0011 219/121.59 |
| 2007/0221582 | A1 | 9/2007 | Holland et al. | |
| 2007/0274858 | A1 * | 11/2007 | Childers | A61L 2/208 422/28 |
| 2008/0014113 | A1 * | 1/2008 | Centanni | 422/27 |
| 2008/0267819 | A1 * | 10/2008 | Bacik | A61L 2/208 422/29 |
| 2011/0027125 | A1 | 2/2011 | Golkowski | |
| 2012/0277662 | A1 | 11/2012 | Golkowski | |
| 2014/0105783 | A1 | 4/2014 | Levsen et al. | |
| 2017/0304476 | A1 | 10/2017 | Taggart et al. | |

FOREIGN PATENT DOCUMENTS

| | | |
|---|---|---|
| EP | 774263 | 5/1997 |
| EP | 906125 | 4/2004 |
| EP | 1557181 | 7/2005 |
| EP | 2525838 | 7/2011 |
| GB | 2371986 | 8/2002 |
| GB | 2371986 A | 8/2002 |
| JP | 4088347 | 3/1992 |
| WO | 8804939 | 7/1988 |
| WO | WO1988004939 | 7/1988 |
| WO | 9105573 | 5/1991 |
| WO | WO1991005573 | 5/1991 |
| WO | 9747331 | 12/1997 |
| WO | WO1997047331 | 12/1997 |
| WO | WO2011/003179 | 1/2011 |
| WO | WO2011/085466 | 7/2011 |
| WO | WO 2011/149188 | 12/2011 |
| WO | WO 2014/123280 | 8/2014 |
| WO | WO 2016/064288 | 4/2016 |
| WO | WO 2017/218832 | 12/2017 |

OTHER PUBLICATIONS

Sadowitz, Benjamin et al., A Novel Non-Thermal Plasma/Free radical Sterilization System for Burn Wound Disinfection, Burn Poster EAST 2013 Compatibility Mode, University of Colorado Denver, Anschutz Medical Campus, College of Engineering and Applied Science in 1 page.

International Search Report and Written For PCT Application No. PCT/US18/57404, dated Jan. 11, 2019 in 13 pages.

* cited by examiner

FREE RADICAL STERILIZATION SYSTEM AND METHOD

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

REFERENCE TO RELATED APPLICATIONS

This *application is a reissue of U.S. Pat. No. 8,758,681, which issued Jun. 24, 2014 from U.S. patent application Ser. No. 13/524,380, filed Jun. 15, 2012, which* is a continuation-in-part of parent patent application Ser. No. 12/510,341, filed Jul. 28, 2009, and entitled "Free Radical Sterilization System and Method"[.], *issued as U.S. Pat. No. 8,221,679, which issued on Jul. 17, 2012.* The aforementioned [application is] *applications and patents are* hereby incorporated herein by reference.

ACKNOWLEDGMENT OF GOVERNMENT SUPPORT

This invention was made with Government support under Grant No. 0750056, awarded by the National Science Foundation, R44DE017831-03 awarded by NIH. The government has certain rights in the invention.

BACKGROUND OF THE INVENTION

1. Field of the Invention

The present invention relates generally to the art of sterilization and decontamination, and more particularly to a system for sterilization of heat sensitive devices. The present invention also relates to a gaseous sterilization process carried out at atmospheric pressure.

2. Description of Related Art

Sterilization methods are used in a broad range of applications, and have used an equally broad range of sterilization agents. As used herein the term "sterilization" refers to the inactivation of bio-contamination, especially on inanimate objects. The term "disinfection" refers to the inactivation of organisms considered pathogenic.

It is known that pulsed or silent electric discharge in air or other gases produces non-thermal plasma. Non-thermal plasma processing involves producing plasma in which the majority of the electrical energy goes into the excitation of electrons. These plasmas are characterized by electrons with kinetic energies much higher than those of the ions or molecules. The electrons in these plasmas are short-lived under atmospheric pressure; instead they undergo collisions with the preponderant gas molecules. The electron impact on gas molecules causes dissociation and ionization of these molecules, which creates a mix of reactive species, in the form of free radicals, ions and secondary electrons. These reactive species cause unique and diverse chemical reactions to occur, even at relatively low temperatures. These chemical reactions are utilized in low temperature decontamination and sterilization technologies.

It is also known to use vaporized hydrogen peroxide (VHP) for sterilization. Known methods of sterilization with VHP include open loop systems, in which the VHP is applied to the items to be sterilized and then exhausted, and closed loop systems, where sterilizing vapors are recirculated.

In a known closed loop system, a carrier gas, such as air, is dried and heated prior to flowing past a vaporizer. A hydrogen peroxide aqueous solution is introduced into the vaporizer and vaporized. The resulting vapor is then combined with the carrier gas and introduced into a sterilization chamber. A blower exhausts the carrier gas from the sterilization chamber and recirculates the carrier gas to the vaporizer where additional VHP is added. Between the sterilization chamber and the vaporizer, the recirculating carrier gas passes through a catalytic destroyer (where any remaining VHP is eliminated from the carrier gas), a drier, a filter and a heater.

United States Patent Application Publication No: US 2005/0129571 A1 by Centanni discloses a closed loop sterilization system. The purpose of using the closed loop is the increase of the free radical concentration in the circulating effluent. Centanni teaches that there should be a VHP (vapor hydrogen peroxide) destroyer employed in the loop. Cetanni teaches that the ozone is mixed with the hydrogen peroxide vapor and the vapor is produced by injecting hydrogen peroxide water solution on a hot plate and thus evaporating it.

SUMMARY OF THE INVENTION

The present invention provides a method and system for sterilization. Free radicals are generated using a plasma electric discharge generator and/or a hydrogen peroxide vaporizer to produce highly bactericidal gaseous effluent. The effluent passes through a chamber, and then is recirculated in a closed loop system. The chamber can be in the form of a tumbler to sterilize items like surgical masks or fabrics or medical waste, or in the form of a stationary chamber for more solid items. A blower may be provided inside the chamber to create turbulence.

For use in pre-heating and drying the items to be sterilized, an input conduit equipped with a valve, heater and filter can supply fresh air to the system and an exhaust blower with an upstream filter and a free radical neutralizer can be used to remove moisture and active radicals from the system. The exhaust blower may be operated at a low speed mode during sterilization to create a negative-pressure condition in the chamber.

A novel multi-output blower can be used to apportion flow in the closed loop, and also to provide multiple outlets to sterilize multiple items or to feed multiple chambers.

The invention can also be used with a wound chamber to aid healing by providing effluent to a wound.

The invention also presents a method of sterilizing items using the above-described apparatus. The method includes placing the items in the chamber, pre-heating and drying them in an open-loop, disinfecting using a closed loop circulating system to supply bactericidal free radicals generated by an electric discharge with free radicals in antimicrobial liquid to the chamber, then flushing and drying the system in an open-loop.

DETAILED DESCRIPTION OF THE INVENTION

Figure 10:
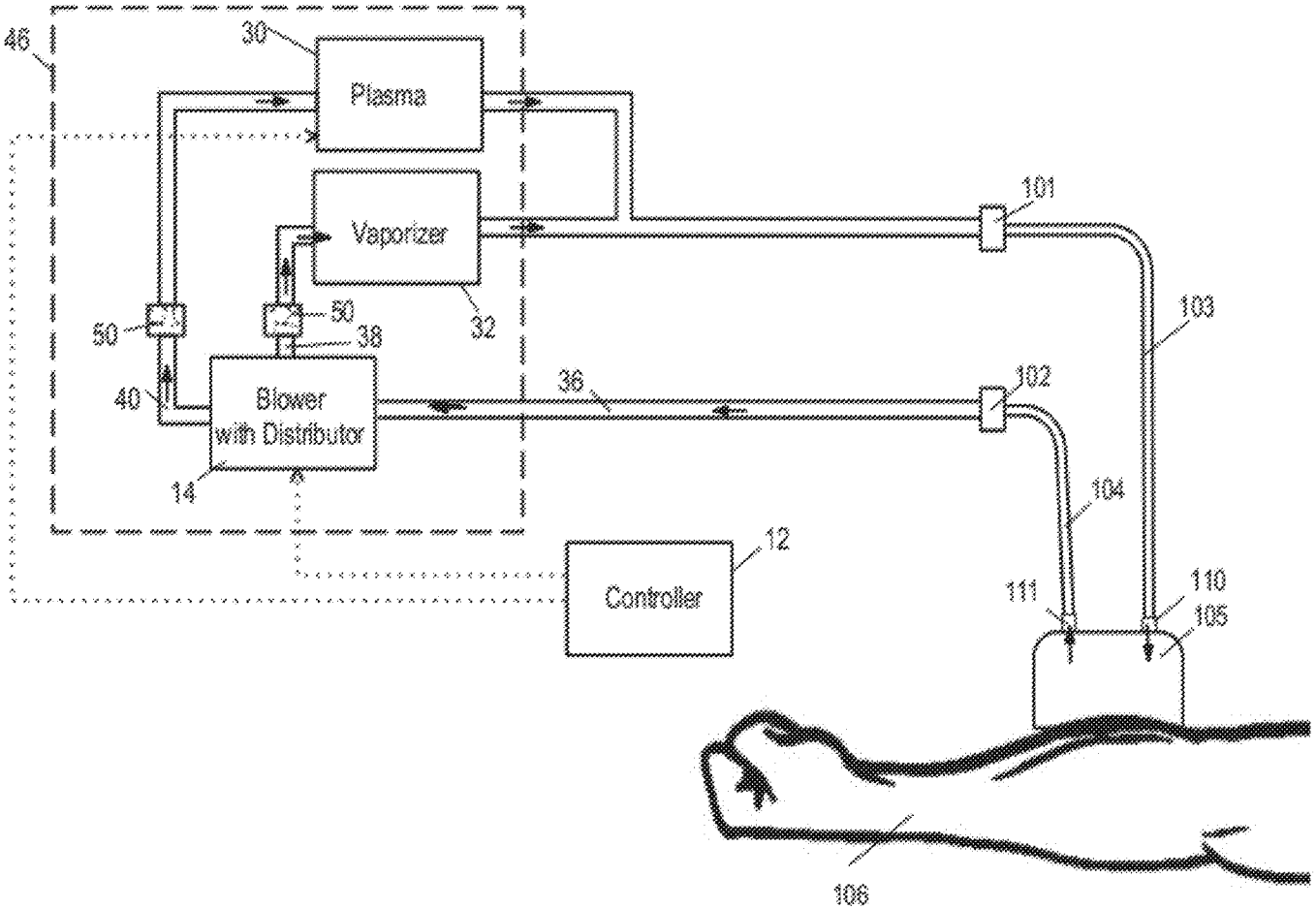
FIG. 10 shows a fourth embodiment of the invention, showing use of the invention with a wound chamber.
Figure 11:
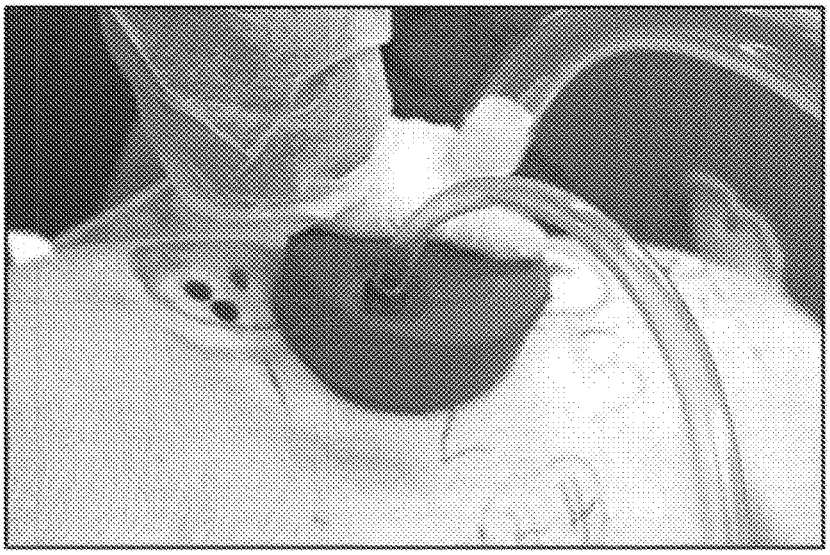
FIG. 11 shows a picture of a wound chamber in use.
Figure 12:
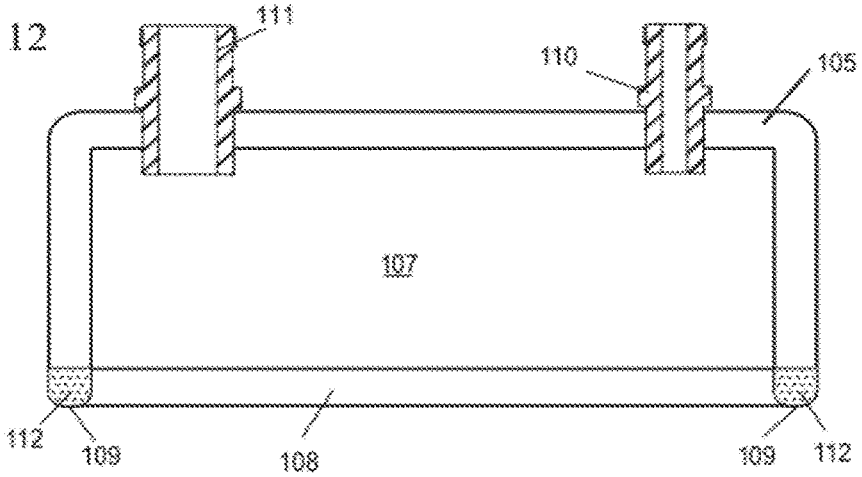
FIG. 12 shows a cut-through side view of a wound chamber.

FIGS. 1 and 2 and 4 through 7 show block diagrams of a sterilization system, illustrating five embodiments of the present invention which use a sterilization chamber. FIGS. 10 to 12 show an additional embodiment using a wound chamber.

In the detailed description below, t will be understood that those parts of the invention which are in common between the various figures are given the same reference number in each figure, and will not be separately discussed in the detailed description of each figure.

Broadly stated, system utilizes a combination of broad mixture of free radicals used in sterilizing and decontamination devices to sterilize items placed in the sterilization chamber, or over which the wound chamber is placed.

First Embodiment—Rotating Chamber with both plasma and vapor.

Figure 1:
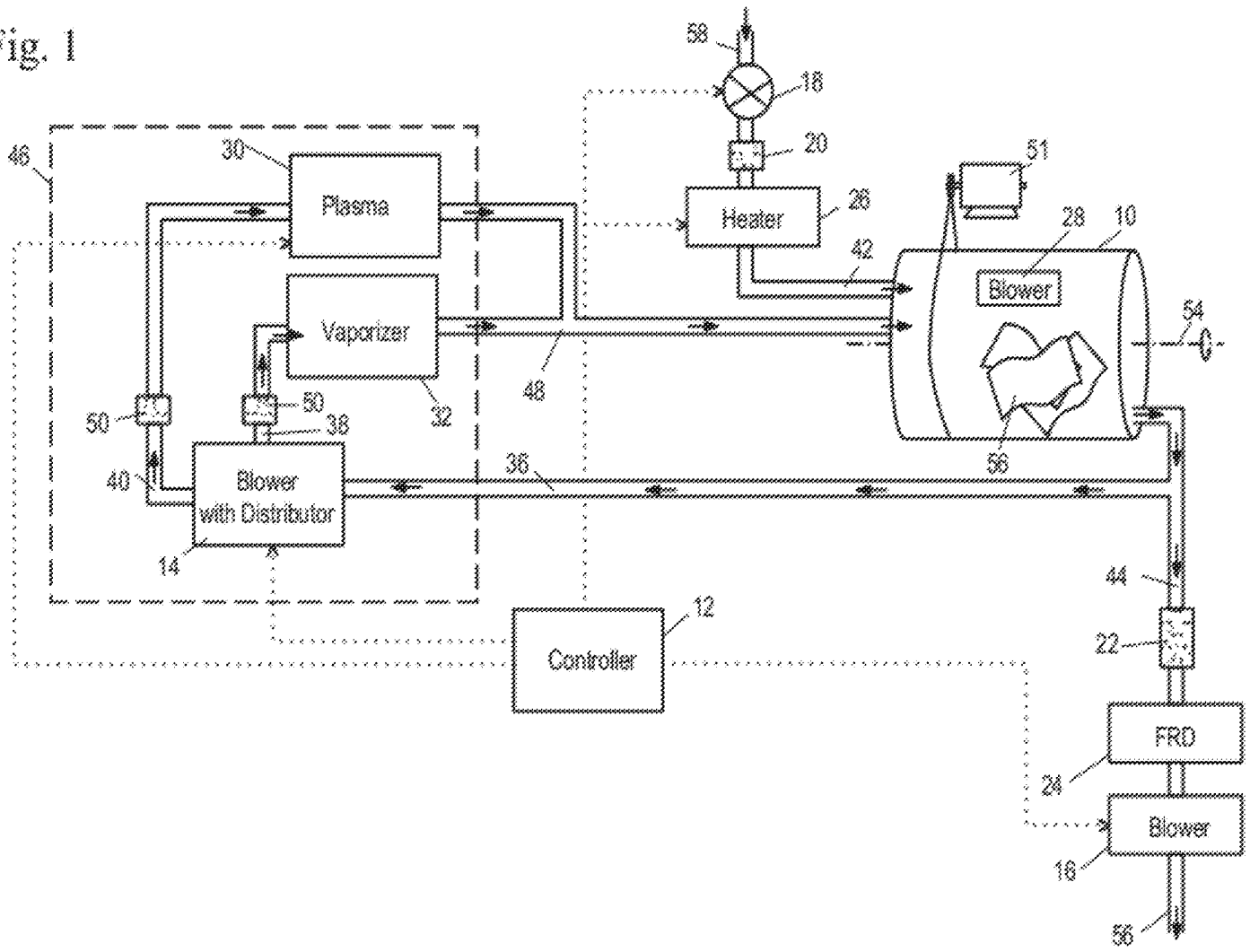
FIG. 1 shows a block diagram of a first embodiment of the invention with a tumbler-type chamber.

In FIG. 1, the chamber 10 is shown as a tumbler-type chamber, which is rotated around a longitudinal axis 54, for example by motor 51, in the manner of a conventional home clothes dryer. Items to be sterilized are placed in a chamber 10. Such a tumbler-type chamber 10 would be appropriate for fabric items 56 such as towels and cloths, surgical masks and gowns, gloves, etc. The tumbler design could also be used to sterilize shredded medical waste within the teachings of the invention.

An effluent generator 46 is used for production of effluent for sterilization or decontamination of the chamber and its contents and for powering the circulation of effluent in the closed loop, to be described later. The effluent generator 46 includes a blower with flow distributor 14, a plasma electric free radical generator 30 and a vaporizer 32.

The plasma free radical generator 30 can be any kind of dielectric barrier discharge device. A device which can be used within the teachings of the invention is an ozone generator such as, for example, ozone generator cell SY-G20 manufactured by Longma Industrial Zone, Bao'an District, Shenzhen, 518108, P.R.C.

The vaporizer 32 contains liquid sterilizing agent such as hydrogen peroxide solution. The gas entering the vaporizer, in contact with the solution, produces bactericidal effluent. While the invention is described with particular reference to hydrogen peroxide as the sterilizing agent, it will be appreciated that the system is also applicable to other solutions and pure liquids, such as peracetic acid or formalin solution.

The vaporizer 32 can be in the form of a "bubbler", in which the gas passes through a container of liquid, or the vaporizer could use plates or wicks over which the gas passes, as is known in prior-art devices. Preferably, the vaporizer 32 uses a measured amount of sterilizing agent, preferably in a pre-measured cartridge which can be inserted into the vaporizer, such that the agent is substantially or completely consumed in the course of a sterilizing run. The vaporizer can thus supply a specific small amount of hydrogen peroxide to the evaporator from a cartridge which is empted and dried during the sterilization process. The drying of the cartridge is accomplished by heating it using a small heater and a limited filtered air flow through the cartridge into the system. This way there is no danger that hydrogen peroxide liquid is present in the cartridge at the end of the cycle when a person/operator will insert a new cartridge for next cycle.

The blower with the flow distributor 14 takes recirculated effluent from the chamber 10 via conduit 36, and distributes it proportionally through conduit 40, which is coupled, optionally through a filter 50, into the plasma generator 30, and through conduit 38, again through optional filter 50, into vaporizer 32. The recirculated effluent is preferably distributed in proportions of approximately 30% to conduit 40, and approximate 70% to conduit 38, although other proportions could be used within the teaching of the invention.

With the proportions noted above, most of the recirculated effluent bypasses the plasma generator 30, passing only through vaporizer 32. The lesser proportion of the effluent passes through plasma generator 30, picking up new free radicals, and is mixed back in the rest of the effluent from the vaporizer 32 at junction 48.

The effluent produced in the effluent generator 46 is then introduced into the chamber 10, completing the closed loop of the system.

In addition to the closed loop system, an open loop system is also provided for the purpose of pre-heating and drying the chamber 10 before and after the circulation of bactericidal effluent through the closed loop system. The open loop system uses a blower 16, exhausting to atmosphere 56, to draw air from an air input 58 through input valve 18 and heater 26 into chamber 10. The input air may be filtered by filter 20, which is preferably of the high efficiency particulate air (HEPA) variety.

The heated, preferably filtered, air is introduced into the chamber 10 through conduit 42.

In the open-loop operation mode, the output of the chamber 10 is drawn out by blower 16 and passes through conduit 44 and a Free Radical Destroyer (FRD) 24, which destroys any free radicals which might remain before the air is exhausted 56. A second filter 22, again preferably of the HEPA type, can be provided in conduit 44 to filter out any particles which would otherwise enter the FRD or be exhausted to the atmosphere. The presence of HEPA filters 20 and 22 at the input and exhaust ensures that there is no microorganism transfer between the ambient air and the sterilization system and vice versa.

The simplest FRD is an activated carbon filter, for example, the Vent Pure "D" from General Carbon Corp. of Paterson, N.J.

By opening valve 18 and turning on heater 26 and blower 16, the chamber 10, and items 56 within the chamber, can be dried and pre-heated before the closed loop operation is begun. Once the pre-heating and drying step is completed, valve 18 is closed and heater 26 is turned off Preferably, blower 16 is of a controllable-speed type, so that it may be operated at a reduced speed during closed-loop operation. This will induce a slight negative pressure in the chamber 10, preventing leakage of effluent from the chamber. However, the blower could be a single-speed blower, in which case it would be turned off after the pre-heating step.

After pre-heating, the system is operated in closed-loop mode by starting blower/distributor 14 and plasma generator 30. The effluent mixture circulates continuously through the loop, from generator 46 through conduit 34, through chamber 10 and conduit 36, back to the generator 46.

When this cycle is finished plasma generator 30 is turned off, valve 18 is opened, and blower 16 is turned on full speed in order to remove the active free radicals from the effluent using FRD 24, and to dry the chamber 10 and the sterilized equipment 56 or 62.

The closed loop blower/distributor 14 may remain on, if desired, so as to circulate air through the closed loop to dry the free radical source 46 and vaporizer 32. Heater 26 may optionally be turned on at this stage, as well, so that heated air is circulated through the vaporizer in order to evaporate residual remains of liquid solution of hydrogen peroxide. Alternatively, blower/distributor 14 may be turned off if it is not desired to circulate air through the closed loop portion of the system during this drying step.

A controller 12 is provided in order to control the operation of the various parts of the system.

Variations on the First Embodiment plasma or vaporizer only and no pre-heater

Figure 4:
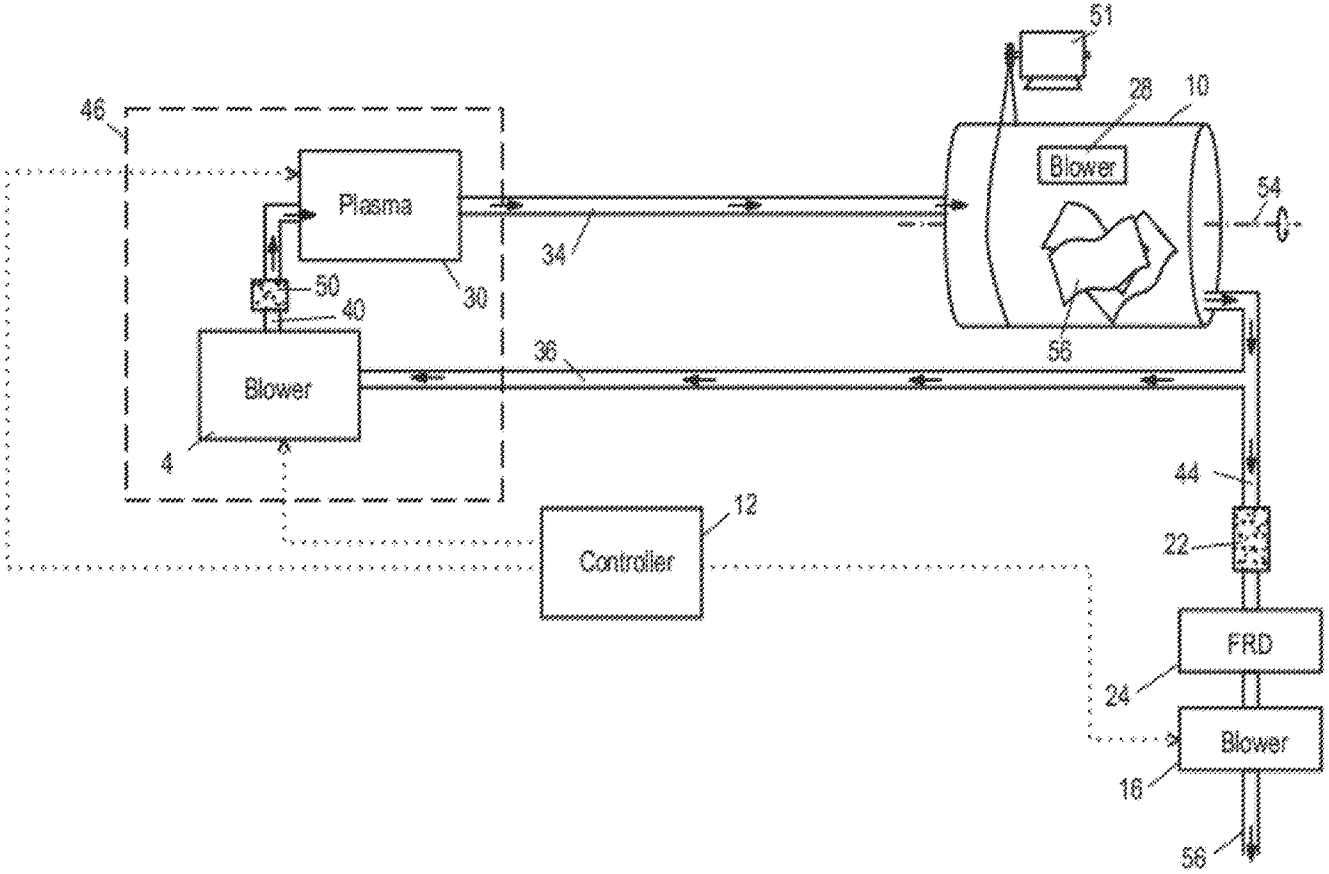
FIG. 4 shows a block diagram of a variation on the embodiment of FIG. 1, omitting the preheater, distributor and vaporizer.
Figure 5:
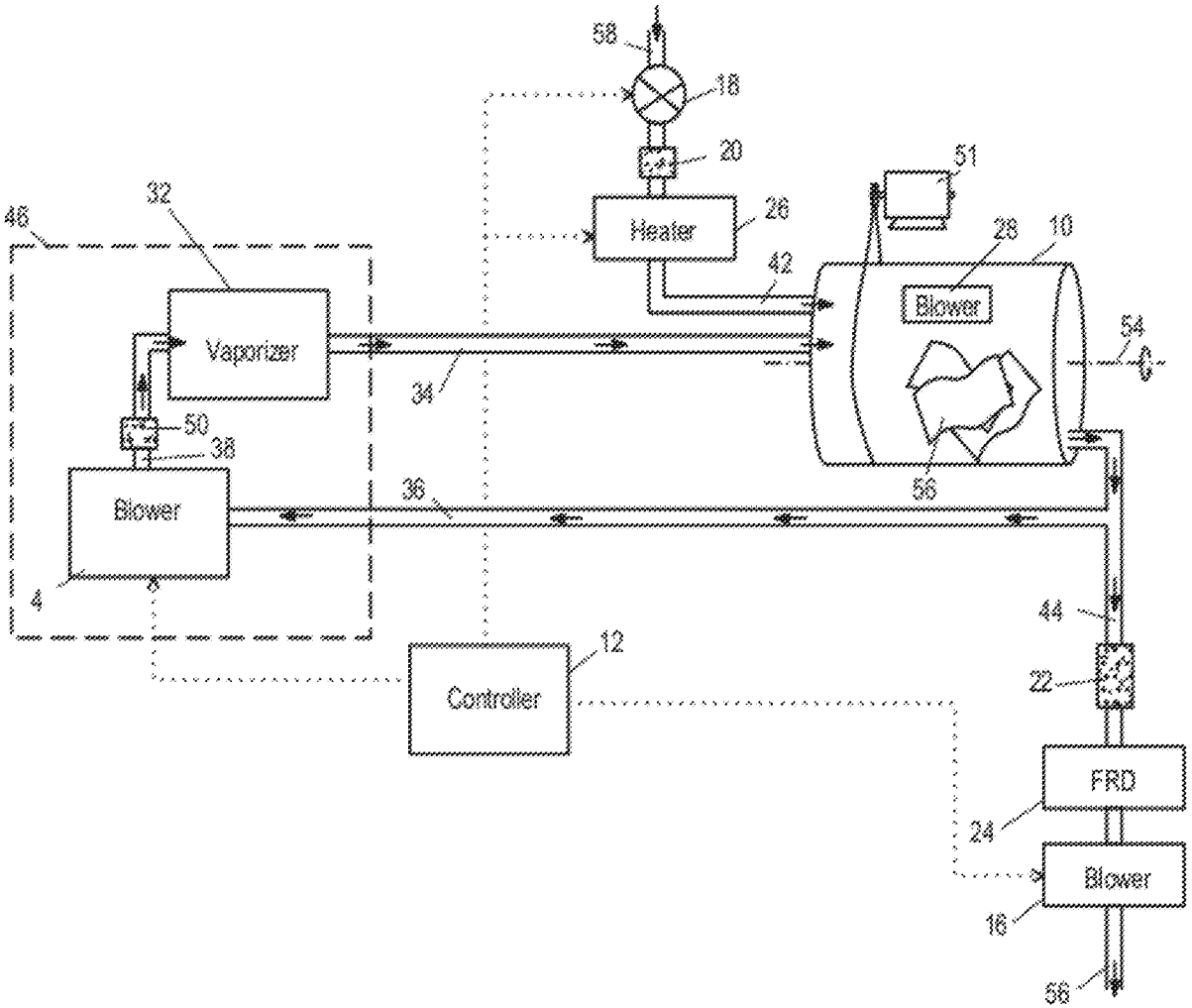
FIG. 5 shows a block diagram of a variation on the embodiment of FIG. 1, omitting the distributor and plasma generator.

As shown in FIGS. 4 and 5, in two variations on the first embodiment of the invention, the effluent generator 46 could be made with only one of the sources—either a plasma generator 30 (FIG. 4) or a vaporizer (FIG. 5). In these variations, the blower/distributor 14 from FIG. 1 is replaced by a blower 4, since with only one source there is no need for distribution.

In FIG. 4, the open loop pre-heater system with its heater 26, filter 20 and valve 18 is omitted as well, to illustrate a variation where there is no pre-heat capability.

It will be understood that these variations could also be applied to the second embodiment, although this is not explicitly illustrated in a figure.

In either of the variations, and in all of the embodiments, the sterilizer of the invention operates in the closed-loop mode by recirculating the effluent through the chamber and the effluent generator without passing the effluent through a free-radical destroyer in the closed loop.

Second Embodiment—Fixed Chamber with both plasma and vapor.

Figure 2:
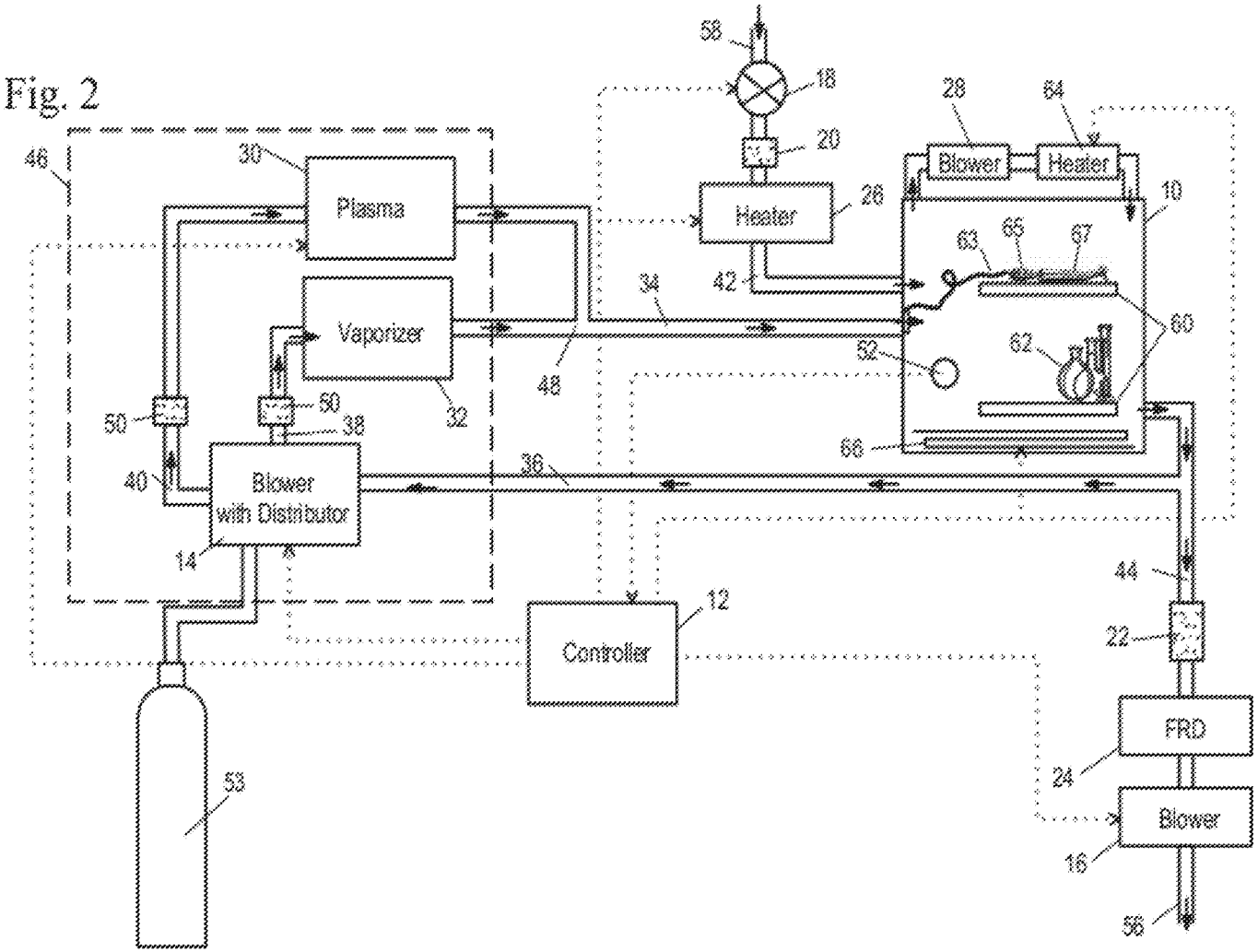
FIG. 2 shows a block diagram of a second embodiment of the invention with a stationary chamber with heating.

FIG. 2 illustrates an embodiment appropriate for more rigid items 62, such as laboratory glassware, surgical implements, dental tools, etc. The items 62 may be put on shelves 60, the shelves preferably being made of wire or perforated to allow free circulation of effluent around the items 62.

For the sterilization of instruments with internal conduits or lumens such as endoscopes or dental handpieces 67, a portion of the sterilant gas can be forced through the instruments 67, while the outer surfaces of the instruments 67 are sterilized by the effluent in the chamber, as discussed below. To do this, one or more additional conduits can be supplied with sterilant gas from the effluent input conduit 34—this is shown in FIG. 2 as flexible hose 63. The hose 63 is equipped with one or more appropriate connectors 65 to plug into the handpiece 67.

Additionally a circulating blower 28 can be used to increase effluent turbulence in the chamber. The blower 28 can be placed in the chamber 10, as shown in FIG. 1, or outside, connected to the chamber by ducts, as shown in FIG. 2. A heater 64 can be put in the ducts to heat the air circulated by the blower 28, or, alternatively, the chamber may be directly heated by elements 66 either in the chamber or attached to the walls of the chamber.

In the embodiment of FIG. 2, a temperature sensor 52 is provided in the chamber 10. The controller 12 can then maintain a selected temperature in the chamber 10 by reading the temperature through sensor 52 and controlling chamber heaters 64 and/or 66 as needed.

Optionally, a carrier gas 53, such as air, oxygen, nitrogen, carbon dioxide, helium, argon, or a combination of carrier gases, can be introduced into the effluent generator 46 to be mixed with the effluent in the closed system. This can be done as an additional input to blower/distributor 14, as shown in FIG. 2.

Third Embodiment

Using centrifugal multiple-outlet blower

Figure 6:
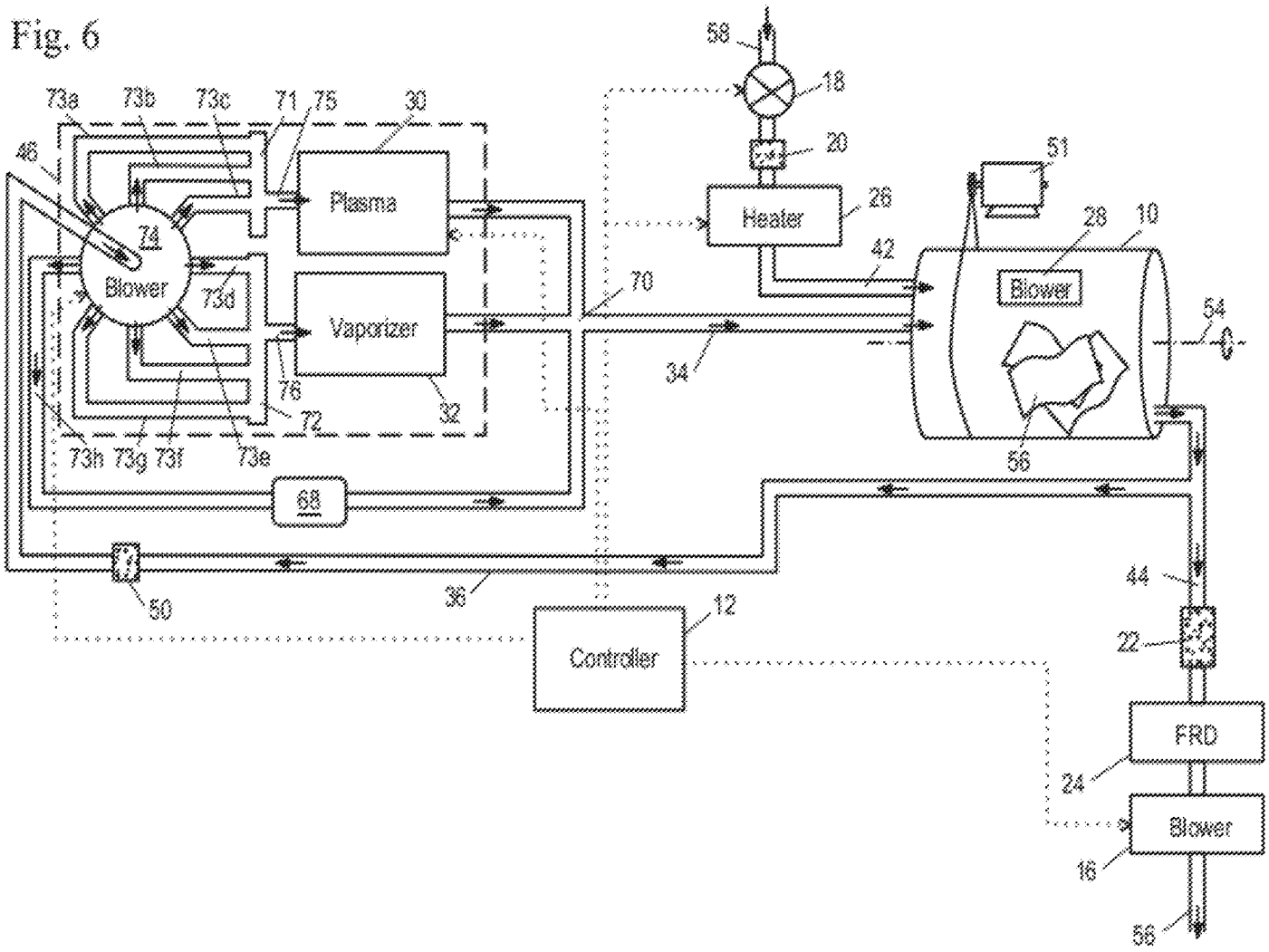
FIG. 6 shows a block diagram of a third embodiment of the invention, using a centrifugal multiple-outlet blower in place of the blower-distributor and adding a bypass heater.
Figure 7:
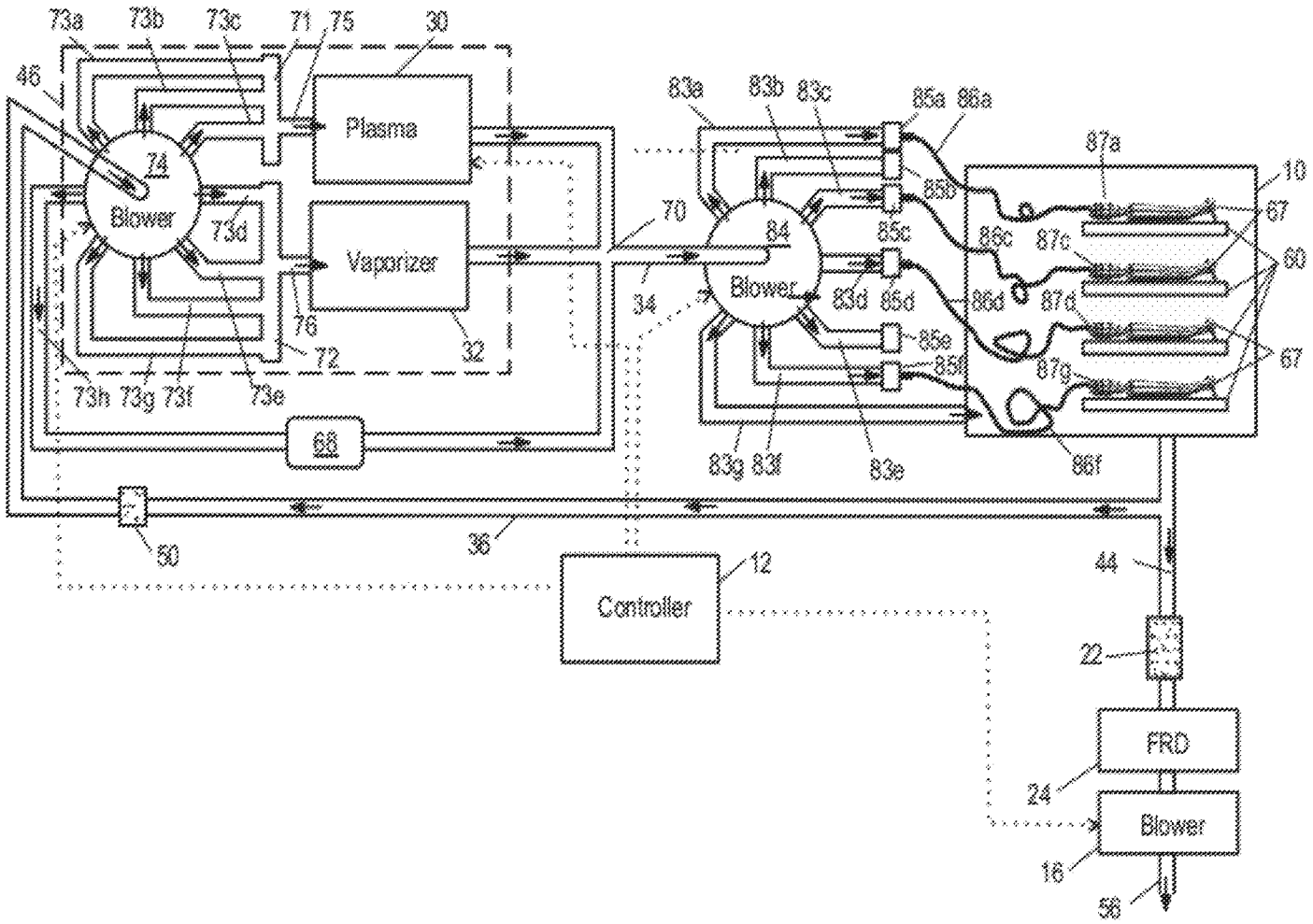
FIG. 7 shows a variation on the embodiment of FIG. 6, using two centrifugal multiple-outlet blowers to provide multiple outlets for recirculation.
Figure 8:
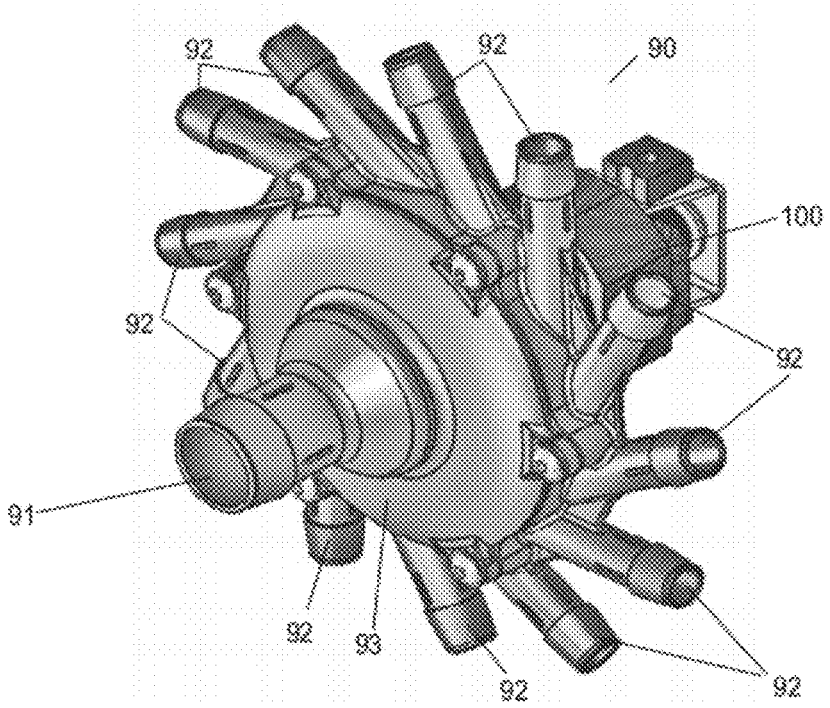
FIG. 8 shows a centrifugal multiple outlet blower as used in the embodiment of FIGS. 6 and 7.
Figure 9:
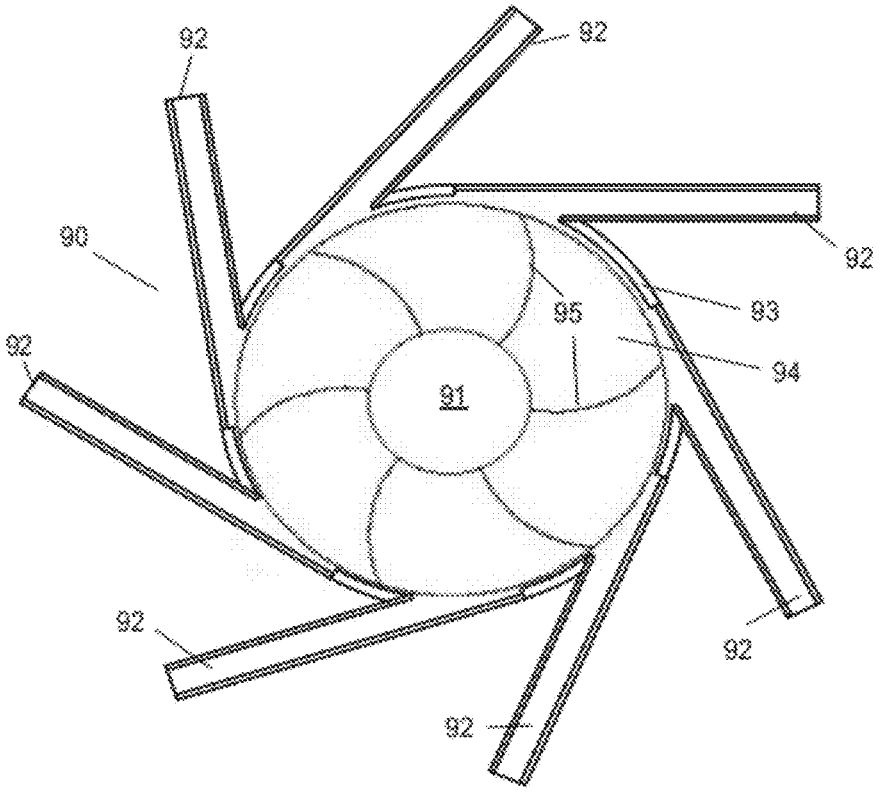
FIG. 9 shows a cut-away diagram of the blower of FIG. 8.

FIGS. 8 and 9 show a multiple-output centrifugal blower which is used with the third embodiment of the invention as shown in FIGS. 6 and 7. The centrifugal blower used in this embodiment is a novel development on the centrifugal blowers and "squirrel-cage"type blowers of the prior art.

As can be seen in FIGS. 8 and 9, the blower 90 has a central input 91 for drawing gas to be distributed by the blower 90 into the blower housing 93. A plurality of tangential outputs 92 are provided, each output providing a stream of gas in approximately equal amounts. The number of outputs 92 can vary within the teachings of the invention, depending on the requirements of the design. As examples, twelve outputs are shown in FIG. 8 and seven in FIG. 9, while blower 74 in FIGS. 6 and 7 has eight outputs and blower 84 has seven outputs.

A central impeller 94 inside the housing 93 is rotated by a conventional motor 100. The motor can be electric, or powered by hydraulic fluid or compressed air, or any other motive force known to the art. The impeller 94 is here shown as centrifugal impeller" type, which has a plurality of curved blades 95. As the impeller 94 is rotated at high speed, air from input 91 is flung outward by centrifugal force and the action of the blades 95, and is expelled through tangential outputs 92.

FIG. 6 shows how a multiple-output blower can be used within the teachings of the invention as the blower-distributor 14 of FIG. 1.

In this embodiment, the effluent generator 46 uses multiple-output blower 74 to apportion the effluent returning from chamber 10 through conduit 36 between the plasma generator 30, the vaporizer 32, and a bypass heater 68. The outputs of the plasma generator 30, vaporizer 32 and bypass heater 68 are combined together at a junction 70, the combined effluent streams flowing into the chamber 10 through conduit 34 as in previous figures.

Because the outputs 73a-73h of the blower 74 each carry an output flow which is a fraction of the total output flow of the blower approximately equal to the total flow divided by the number of outlets. Therefore a desired portion of the effluent can be chosen by combining an appropriate choice of the number of outputs, with the output of the manifold being approximately equal to the number of blower outputs being combined divided by the total number of outlets available. Multiple outputs can be combined using manifolds, such as manifold 71 to which outputs 73a-73c are input, or manifold 72 which combines the flow from outputs 73d-73g. Output 73h is connected directly to the bypass heater 68.

In the example of FIG. 6, blower 74 has eight outputs 73a-73h, so each output carries approximately one eighth or 12.5% of the total output of the blower. Therefore, in the arrangement of this example, manifold 71 receives three eighths (37.5%) of the flow, and the output of the manifold feeds this flow to plasma generator 30 through conduit 75. Similarly, manifold 72 receives four eighths (or one half) (50%) of the flow through conduit 76, the output of which is connected to vaporizer 32. Bypass heater 68 receives one eighth (12.5%) of the flow directly from a single output 73h, which could be thought of as a manifold with a single input.

FIG. 7 shows the third embodiment used with a fixed chamber for sterilizing items such as dental handpieces 67 (or other medical tools having lumens or other interior conduits or spaces which should be sterilized), as in the second embodiment of FIG. 2. Shelves 60 can be provided to support the tools 67, as needed.

In FIG. 7, rather than feeding the chamber 10 directly, the effluent conduit 34 is used to feed a second multiple-outlet centrifugal blower 84. In this variation, the multiple outputs 83a-83g of blower 84 are used individually to feed multiple users of the effluent, rather than being combined to apportion flow as with outputs 73a-73h of blower 74.

The outputs 83a-83f of blower 84 are fitted with shut-off valves or quick-disconnect fittings 85a-85f, of any kind known to the art. Flexible hoses 86a-86f are plugged into fittings 85a-85f to conveys effluent from the fittings 85a-85f to connectors or adaptors 87a-87f, into which the handpieces 67 can be plugged to sterilize the insides of the handpieces. Output 83g of blower 84 is routed directly to chamber 10, to supply effluent to the chamber for sterilizing the outside of the handpieces 67, as well as any other contents of the chamber.

Fourth Embodiment

The Wound Chamber

FIGS. 10-12 show how the invention can be used with an open-sided portable wound chamber 105 to apply effluent to an open wound on a patient. Such application has been shown in experiments to promote healing.

FIG. 10 shows how the system of the invention is used in this application. Effluent generator 46 recirculate effluent from conduit 36 to conduit 34, as described in the preceding embodiments. It will be understood that while the effluent generator 46 is shown in FIG. 10 in the version used in FIGS. 1 and 2, the effluent generator 46 could also be any of the other versions described herein or in parent patent application Ser. No. 12/510,341, incorporated herein by reference.

The wound chamber 105 is shown in FIG. 12 in a sectional view. The chamber 105 has a body 107 with an open bottom 108. The edges 109 around the open bottom 108 can be simply rounded off, or could be provided with flexible or resilient sealing material 112 to facilitate a tight seal against a surface. Connectors 110 and 111 provide means for connecting input and output hoses, respectively, to route the flow of effluent to and from the chamber. The connectors could be the same size, or, as shown in FIG. 12, the input connector 110 could be of smaller diameter than the output connector 111.

In this embodiment, the output conduit 34 of the effluent generator feeds a wound chamber 105 through a flexible hose 103 which connects to appropriate connectors 101 and 110 at each end. Return effluent from the wound chamber 105 passes through flexible hose 104 with connectors 102 and 111 into return conduit 36, to be recirculated back through the effluent generator 46. In use, the chamber 105 is placed upon the body of the patient (here shown as an arm 106), over the wound to be treated. The chamber 105 is pressed firmly against the body 106, and the sterilizer is operated for a selected period of time.

EXAMPLE

Use of the Sterilizer and Wound Chamber

FIG. 11 shows a photograph of the wound chamber in use in an experiment on a pig. In the example, multiple deep dermal partial thickness burn injuries were induced in Yorkshire pigs weighing 40-45 kilograms. After the burn wounds were produced, the wounds were inoculated with both Staphylococcus aureus and Pseudomonas aeruginosa to create a polymicrobial wound infection. These microorganisms were chosen as these two organisms are commonly found in infected burn wounds in humans.

Figure 13:
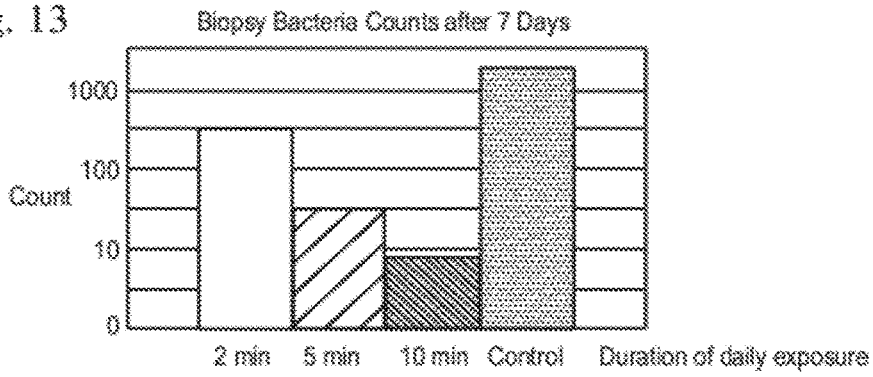
FIG. 13 shows a bar graph of results from a method of wound treatment using the fourth embodiment of the invention.

Burn wounds were exposed to disinfecting effluent produced by the sterilizer of the invention by placing the wound. chamber over the wounds and operating the sterilizer for 2, 5 and 10 minutes each day for seven days. The wounds were examined on a daily basis. The results of the seventh day bacterial count compared with the control (not treated) are shown in FIG. 13, which has a logarithmic scale of bacteria count on the vertical axis, and bars along the horizontal axis showing counts in areas exposed for 2 minutes, 5 minutes and 10 minutes, as well as a bar showing counts in an untreated (control) area. As can be seen in this figure, the bacteria counts are significantly lower in areas treated using the invention—the ten-minute treatment count being more than 100 times smaller than the control.

Method of Operation

Figure 3:
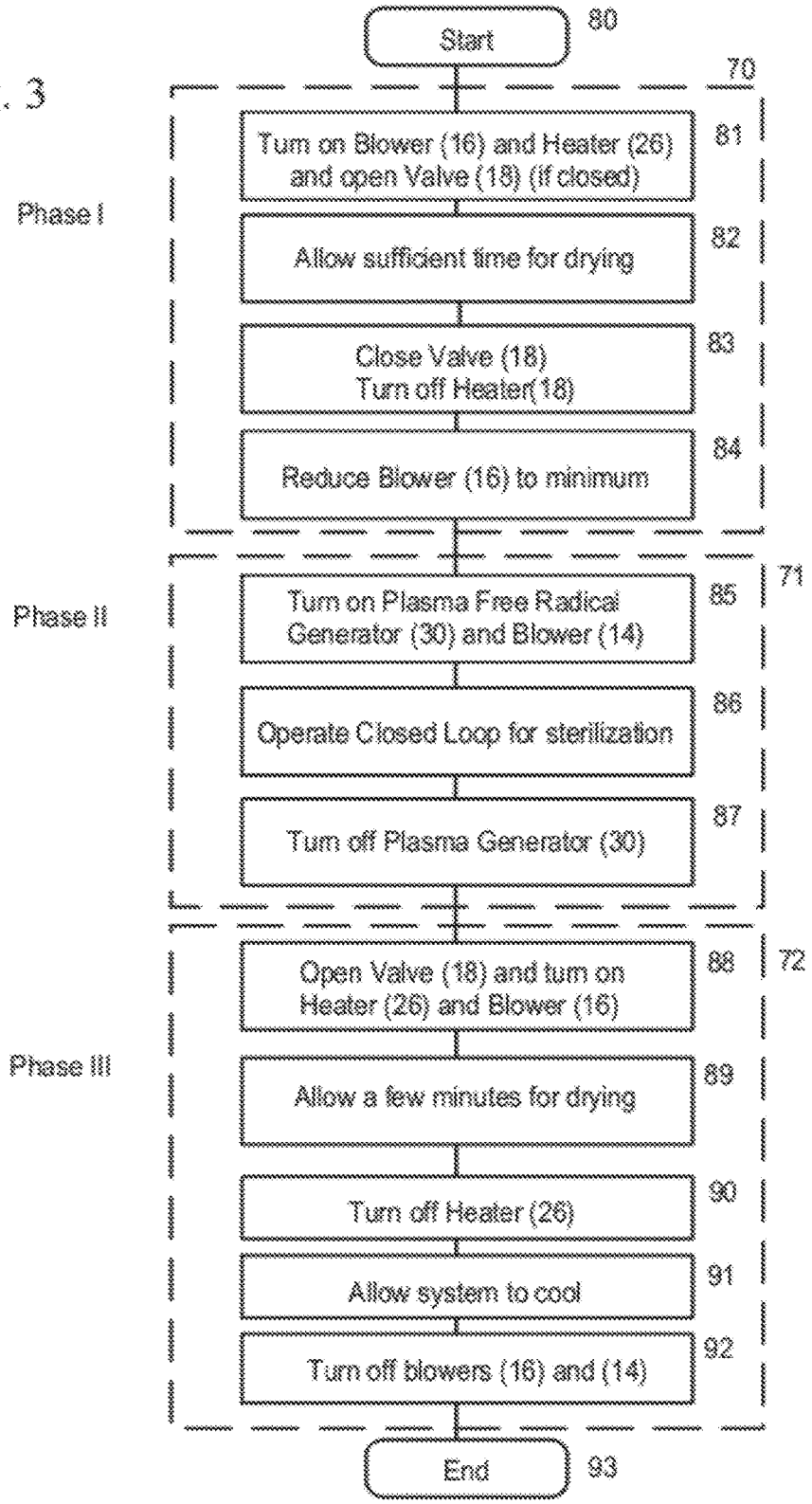
FIG. 3 shows a flowchart of the method of the invention

As shown in FIG. 3, the sterilization process using the embodiments of the invention which have pre-heaters and.or exhaust systems, consists of up to three phases:

80—Start the method

70—Phase I—Pre-sterilization drying and heating (Open Loop)

- 81—During this phase the exhaust blower 16 is turned on, the valve 18 is opened (if closed) and the heater 26 is turned on. This causes fresh air from the inlet 58 to flow through valve 18, optional HEPA filter 20, and heater 26 into chamber 10 via conduit 42. The heated air dries and heats the sterilized items and is expelled through conduit 42 via optional filter 22, free radical destroyer 24 and exhaust blower 16.
- 82—The drying and heating is continued for a sufficient time, for example approximately 5 minutes. If desired, a heat sensor or humidity sensor (not shown) could be provided at the exhaust 56 or in conduit 44, coupled to the controller 12, so that the duration of the pre-heating could be controlled based on empirical data rather than an arbitrary elapsed time. Optionally, if a chamber temperature sensor 52 is provided, the controller 12 may operate heater 26 and, if provided, chamber heaters 64 and/or 66 to maintain a desired pre-heat temperature in the chamber.

83—After the chamber and the sterilized items are dried and heated the input valve 18 is closed.

84—The exhaust blower 16 is turned off (or reduced to minimum speed, if this ability is available)

71—Phase II—Sterilization (Closed Loop)

85—The plasma generator 30 and the closed loop blower/distributor 14 are turned on. This causes the air to circulate in the closed loop through the free radical generator 46 and the chamber 10, as described in the description of the apparatus, above.

86—The closed loop system produces continuously free radical rich effluent that sterilizes items in the chamber 10. The closed loop operation continues for a time sufficient for sterilization. As an example, a duration of approximately 20-30 minutes should be sufficient for adequate sterilization of most items, If provided, the controller 12 will activate chamber heaters 64 and/or 66 to maintain a desired temperature in chamber 10, as measured by sensor 52.

87—At the end of the sterilization period, the plasma generator 30 is turned off

72—Phase III—Post-sterilization drying and clearing (Open Loop)

88—Input valve 18 is opened, heater 26 is turned on and the exhaust blower 16 is turned on. The closed loop blower/distributor 14 may remain on during, this Phase III in order to dry free radical source 46, or, if desired, blower/distributor may be turned off in step 87. The air flows from the input 58 via conduit 42 into the chamber 10 drying the items and, if blower 14 remains on, the free radical source 46. The moist air is expelled into the atmosphere via filter 22 and free radical destroyer 24.

89—The open loop operation is maintained for a time sufficient to dry and clear the chamber 10. A period of, for example, five minutes should suffice.

90—Heater 26 is turned off, with blower 16 (and blower 14, if desired) remaining on.

91—Fresh air is passed through the system for a sufficient time to cool down to the ambient temperature. For example, a few minutes operation would suffice for cooling. Optionally, if sensor 52 is provided in the chamber, the controller 12 could be programmed to continue this cooling until a desired temperature is reached.

92—Blower 16 is turned off, as well as blower 14 if it is still on. Valve 18 may be closed at this time, or left open for the next run.

93—The method ends. The chamber 10 may now be opened and the items 56/62 removed. New items may be put in the chamber, if desired, and the process repeated again from 80.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention. The drawings are for the purpose of illustrating embodiments of the invention only, and not for the purpose of limiting it.

What is claimed is:

1. A free radical sterilization system comprising:

a) a chamber for containing items to be sterilized;

b) an effluent generator having an input coupled to the chamber and an output coupled to the chamber for closed-loop circulation, comprising:

i) a blower/distributor comprising a blower having an input coupled to the input of the effluent generator and at least one output, and a flow distributor for distributing blower flow from the at least one output of the blower to at least a first output and a second output in selected portions;

ii) a plasma electric free radical generator having an input coupled to the first output of the blower/distributor and an output coupled to the output of the effluent generator; and iii) a vaporizer having an input coupled to the second output of the blower, and an output coupled to the output of the effluent generator, the vaporizer contacting, a liquid sterilizing agent with the output of the blower/distributor to produce bactericidal effluent at the output of the vaporizer;

such that bactericidal effluent from the effluent generator flows through the chamber and back through the effluent generator in a closed loop without an intervening free-radical destroyer.

2. The free radical sterilization system of claim 1, further comprising:

c) an open loop pre-heater and dryer comprising:

i) an input valve having an input open to atmosphere and an output;

ii) a heater having an input coupled to the input valve and an output coupled to the chamber; and iii) an exhaust blower having an input coupled to the chamber and an output exhausting to atmosphere;

such that air is taken in through the input valve, heated by the heater, passes through the chamber and is exhausted to atmosphere in an open loop.

3. The free radical sterilization system of claim 1, in which the chamber comprises a tumbler.

4. The free radical sterilization system of claim 1, in which the chamber comprises a wound chamber having an open bottom surface.

5. The free radical sterilization system of claim 1, in which the liquid sterilizing agent is hydrogen peroxide.

6. The free radical sterilization system of claim 1, in which the vaporizer contains a determined amount of liquid sterilizing agent at a beginning of a sterilization run.

7. The free radical sterilization system of claim 1, in which the flow distributor of the blower/distributor distributes 30% of the flow to the first output and 70% to the second output.

8. The free radical sterilization system of claim 1, in which the blower/distributor comprises:

a) a multiple-output centrifugal blower having an input coupled to the input of the effluent generator and a plurality of outputs, each of the plurality of outputs of the multiple-output centrifugal blower having an output flow which is a fraction of a total output flow of the multiple-output centrifugal blower approximately equal to the total flow divided by the number of outputs in the plurality of outputs; and b) a flow distributor comprising at least:

i) a first manifold having a plurality of inputs coupled to a first selected number of the plurality of outputs of the multiple-output centrifugal blower and an output comprising the first output of the blower/distributor; and ii) a second manifold having a plurality of inputs coupled to a second selected number of the plurality of outputs of the multiple-output centrifugal blower and an output comprising the second output of the blower/distributor;

such that the portion of the total flow at the first output of the blower/distributor is equal to the sum of the fractions of the total output flow multiplied by the first selected number; and the portion of the total flow at the first output of the blower/distributor is equal to the sum of the fractions of the total output flow multiplied by the second selected number.

9. The free radical sterilization system of claim 8, in which at least one output of the multiple-output centrifugal blower is coupled to the chamber through a heater.

10. The free radical sterilization system of claim 1, further comprising a multiple-output centrifugal blower having an input coupled to the output of the effluent generator and a plurality of outputs, at least one of the plurality of outputs being coupled to the chamber.

11. The free radical sterilization system of claim 10, in which a plurality of the outputs from the multiple-output centrifugal blower further comprise fittings for coupling hoses for connection to objects in the chamber, such that effluent from the plurality of outputs passes through the fittings and the hoses and an inside of the objects to the chamber.

12. The free radical sterilization system of claim 1, further comprising a circulating blower for inducing turbulent flow within the chamber.

13. The free radical sterilization system of claim 1, further comprising a chamber heater, directly heating the chamber.

14. The free radical sterilization system of claim 1, further comprising a controller coupled to the blower/distributor of the effluent generator and the plasma electric free radical generator.

15. The free radical sterilization system of claim 1, further comprising a source of carrier gas coupled to the closed loop.

16. The free radical sterilization system of claim 1, further comprising a conduit for sterilizing interior passages in an instrument, having a first end coupled to the output of the effluent generator and a second end in the chamber having a connector for coupling with the instrument, so that a portion of the effluent passes through the internal passages in the instrument plugged into the connector.

17. A free radical sterilization system comprising:

a) a chamber for containing items to be sterilized;

b) an effluent generator having an input coupled to the chamber and an output coupled to the chamber for closed-loop circulation, comprising:

i) a blower having an input coupled to the input of the effluent generator and an output; and ii) a source of effluent having an input coupled to the output of the blower and an output coupled to the output of the effluent generator, comprising one of a plasma electric free radical generator or a vaporizer having a liquid sterilizing agent;

such that bactericidal effluent from the effluent generator flows through the chamber and back through the effluent generator in a closed loop without an intervening free-radical destroyer*; and*

*c) a multiple-output centrifugal blower having an input coupled to the output of the effluent generator and a plurality of outputs, at least one of the plurality of outputs being coupled to the chamber*.

18. The free radical sterilization system of claim 17, in which the chamber comprises a tumbler.

19. The free radical sterilization system of claim 17, in which the chamber comprises a wound chamber having an open bottom surface.

20. The free radical sterilization system of claim 17, in which the liquid sterilizing agent is hydrogen peroxide.

21. The free radical sterilization system of claim 17, in which the vaporizer contains a determined amount of liquid sterilizing agent at a beginning of a sterilization run.

[22. The free radical sterilization system of claim 17, further comprising a multiple-output centrifugal blower having an input coupled to the output of the effluent generator and a plurality of outputs, at least one of the plurality of outputs being coupled to the chamber.]

23. The free radical sterilization system of claim [22] *17*, in which a plurality of the outputs from the multiple-output centrifugal blower further comprise fittings for coupling hoses for connection to objects in the chamber, such that effluent from the plurality of outputs passes through the fittings and the hoses and an inside of the objects to the chamber.

24. A method of sterilization of items in a sterilization chamber using free radicals, comprising:

a) drying and heating the items in the chamber by drawing heated air through the chamber and exhausting the air from the chamber in an open loop;

b) circulating free radical rich effluent comprising a mixture of free radicals and a sterilizing agent, in a closed loop from an effluent generator, through the chamber, then back through the effluent generator, the effluent generator having an input coupled to the chamber and an output coupled to the chamber for closed-loop circulation, the effluent generator comprising a blower/distributor comprising a blower having an input coupled to the input of the effluent generator at least one output, and a flow distributor for distributing blower flow from the at least one output of the blower to at least a first output and a second output in selected portions; a plasma electric free radical generator having an input coupled to the first output of the blower/distributor and an output coupled to the output of the effluent generator; a vaporizer having an input coupled to the second output of the blower, and an output coupled to the output of the effluent generator, the vaporizer contacting a liquid sterilizing agent with the output of the blower/distributor to produce bactericidal effluent at the output of the vaporizer;

c) turning off the effluent generator at the end of a determined sterilization period;

d) drying and heating the items in the chamber by drawing heated air through the chamber and exhausting the air from the chamber in an open loop; and e) cooling the items in the chamber by drawing ambient air through the chamber and exhausting the air from the chamber in an open loop.

25. The method of claim 24, in which air is exhausted during step b, creating a negative pressure in the chamber.

26. The method of claim 24, in which steps d and e further comprise destroying free radicals before exhausting the air using a free radical destroyer.

27. The method of claim 24, in which step a is maintained for a determined period of time.

28. The method of claim 24, in which step a is maintained until a determined temperature or humidity is measured in the exhaust.

29. The method of claim 24, further comprising circulating the air in the chamber with a circulating blower at least during step b.

30. The method of claim 24, further comprising maintaining a determined temperature in the chamber during step b.

31. A method of treating a wound on a body, using a stream of a free radical rich effluent comprising a mixture of free radicals and a sterilizing agent from an effluent generator having an input and an output for closed-loop circulation, the effluent generator comprising a blower/distributor comprising a blower having an input coupled to the input of the effluent generator at least one output, and a flow distributor for distributing blower flow from the at least one output of the blower to at least a first output and a second output in selected portions; a plasma electric free radical generator having an input coupled to the first output of the blower/distributor and an output coupled to the output of the effluent generator; a vaporizer having an input coupled to the second output of the blower, and an output coupled to the output of the effluent generator, the vaporizer contacting a liquid sterilizing agent with the output of the blower/distributor to produce bactericidal effluent at the output of the vaporizer, using a wound chamber having an open bottom, an input coupled to the output of the effluent generator and an output coupled to the input of the effluent generator, the method comprising:

a) placing the open bottom of the wound chamber on the body around the wound and applying pressure to seal the wound chamber against the body;

b) turning on the effluent generator;

c) for a determined treatment period, circulating the stream of effluent from the output of the effluent generator through the wound chamber and back to the input of the effluent generator in a closed loop;

d) turning off the effluent generator at the end of a determined sterilization period;

e) removing the wound chamber from the body; and f) repeating the method at a determined interval for a determined treatment duration.

32. The method of claim 31, in which the treatment period is at least two minutes.

33. The method of claim 31, in which the treatment period is at least ten minutes.

34. The method of claim 31, in which the determined interval is a day.

35. The method of claim 31, in which the determined treatment duration is one week.

*36. A sterilizing device comprising:*

*a) a chamber for containing items to be sterilized;*

*b) an effluent generator having an input coupled to the chamber and an output coupled to the chamber, comprising:*

*i) a blower/distributor comprising a blower having an input coupled to the input of the effluent generator and at least one output, and a flow distributor for distributing blower flow from the at least one output of the blower to at least a first output and a second output in selected portions;*

*ii) a free radical generator having an input coupled to the first output of the blower/distributor and an output coupled to the output of the effluent generator; and*

*iii) a vaporizer having an input coupled to the second output of the blower, and an output coupled to the output of the effluent generator, the vaporizer contacting a liquid sterilizing agent with the output of the blower/distributor to produce bactericidal effluent at the output of the vaporizer;*

*such that bactericidal effluent from the effluent generator flows through the chamber and back to the effluent generator without an intervening free-radical destroyer.*

*37. A method for sterilizing items, comprising:*

*a) generating a bacteriocidal effluent comprising a mixture of free radicals and a sterilizing agent via an effluent generator,*

*the effluent generator comprising:*

*a blower;*

*a plasma electric free radical generator; and*

*a vaporizer,*

*wherein the vaporizer contacts a liquid sterilizing agent with the output of the blower/distributor to produce said bactericidal effluent; and*

*b) circulating the bacteriocidal effluent through a chamber containing items to be sterilized, wherein the bacteriocidal effluent is circulated in a closed loop between the effluent generator and the chamber, without an intervening free radical destroyer.*

*38. A centrifugal blower for use in a sterilization system, the blower comprising:*

*an air input and a plurality of outputs*

*wherein each of the plurality of outputs has an output flow which is a fraction of a total output flow of the centrifugal blower, the fraction being approximately equal to the total flow divided by the number of outputs in the plurality of outputs;*

*wherein the air input of the blower is coupled to an input of an bacteriocidal effluent generator, wherein the effluent generator is in fluid communication with one or more of: (i) a plasma electric free radical generator and (ii) a vaporizer contacting a liquid sterilizing agent;*

*a flow distributor comprising at least a first manifold having a plurality of inputs coupled to a first selected number of the plurality of outputs of the centrifugal blower and an output comprising the first output of the blower/distributor*

*wherein the total flow at the first output of the blower/distributor is equal to the sum of the fractions of the total output flow multiplied by the first selected number.*

* * * * *